United States Patent [19]
Lackey

[11] Patent Number: 5,282,803
[45] Date of Patent: Feb. 1, 1994

[54] INSTRUMENTATION FOR LONG STEM SURGERY

[75] Inventor: Jennifer J. Lackey, Memphis, Tenn.

[73] Assignee: Smith & Nephew Richards Inc., Memphis, Tenn.

[21] Appl. No.: 859,884

[22] Filed: Mar. 30, 1992

Related U.S. Application Data

[63] Continuation-in-part of Ser. No. 765,379, Sep. 25, 1991, Pat. No. 5,100,408, which is a continuation of Ser. No. 666,262, Mar. 7, 1991, Pat. No. 5,053,037.

[51] Int. Cl.$^5$ .......................... A61B 17/00; A61F 2/32
[52] U.S. Cl. ........................................ 606/80; 606/88; 606/96
[58] Field of Search ................. 606/79, 80, 78, 62, 606/57, 96, 86, 87, 88; 623/16, 17

[56] References Cited

U.S. PATENT DOCUMENTS

| | | | |
|---|---|---|---|
| 4,467,801 | 8/1984 | Whiteside | 606/80 |
| 4,474,177 | 10/1984 | Whiteside | 606/80 |
| 4,487,203 | 12/1984 | Androphy | 128/303 |
| 4,567,885 | 2/1986 | Androphy | 128/92 |
| 4,567,886 | 2/1986 | Petersen | 128/92 |
| 4,590,929 | 5/1986 | Klein | 606/80 |
| 4,646,729 | 3/1987 | Kenna | 606/80 |
| 4,703,751 | 11/1987 | Pohl | 128/92 |
| 4,719,919 | 1/1988 | Marchosky et al. | 128/401 |
| 4,721,104 | 1/1988 | Kaufman et al. | 128/92 |
| 4,722,330 | 2/1988 | Russell et al. | 128/92 |
| 4,736,737 | 4/1988 | Fargie et al. | 128/92 |
| 4,738,253 | 4/1988 | Buechel | 606/80 |
| 4,738,254 | 4/1988 | Buechel et al. | 128/92 |
| 4,759,350 | 7/1988 | Dunn et al. | 128/92 |
| 4,773,407 | 9/1988 | Petersen | 128/92 |
| 4,892,093 | 1/1990 | Zarnowski et al. | 606/82 |
| 4,893,619 | 1/1990 | Dale et al. | 606/87 |
| 4,907,578 | 3/1990 | Petersen | 606/79 |
| 4,926,847 | 5/1990 | Luckman | 606/88 |
| 4,935,023 | 6/1990 | Whiteside et al. | 606/88 |
| 4,952,213 | 8/1990 | Bowman | 606/79 |
| 4,959,066 | 9/1990 | Dunn et al. | 606/89 |
| 5,002,545 | 3/1991 | Whiteside | 606/80 |
| 5,037,423 | 8/1991 | Kenna | 606/86 |
| 5,053,037 | 10/1991 | Lackey | 606/88 |
| 5,100,408 | 3/1992 | Lackey | 606/79 |
| 5,108,405 | 4/1992 | Mikhail | 606/80 |

FOREIGN PATENT DOCUMENTS 0122669 10/1984 European Pat. Off.
685364 12/1939 Fed. Rep. of Germany.

Primary Examiner—Michael A. Brown
Attorney, Agent, or Firm—Pravel, Hewitt, Kimball & Krieger

[57] ABSTRACT

A method and apparatus for installing a knee prosthetic component on a patient's tibia includes the selection by a surgeon of one of a plurality of reamers, each of the reamers having a different cutting size diameter such as for example between ten and twenty-two millimeters of cutting diameter. The reamer is initially selected as a very small reamer and the surgeon places progressively larger cutting diameter reamers in the patient's intermedullary canal until resistance or until the reamer becomes stuck. When the surgeon finds a reamer that is sized so that it will ream and cut cortical bone preferably a full three hundred and sixty degrees (360°), the patient's intramedullary canal is cut and reamed into a depth which corresponds to the length of the stem portion of the femoral prosthetic component. Instrumentation is installed on the upper generally cylindrically shaped portion of the reamer as soon as cutting and reaming is completed and without removal of the reamer from the intermedullary canal. This insures that cutting instrumentation will be properly oriented with regard to the hole that is cut and reamed to prepare the intermedullary canal.

15 Claims, 8 Drawing Sheets

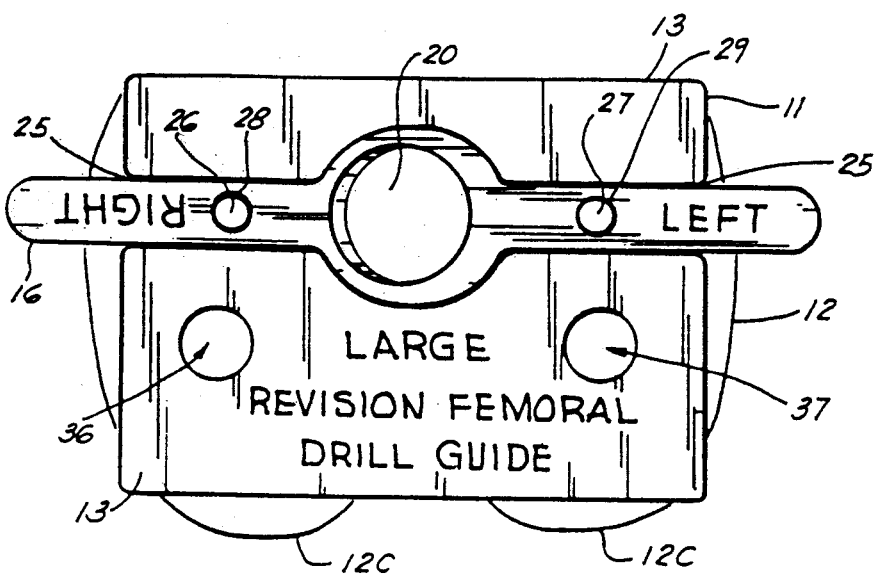
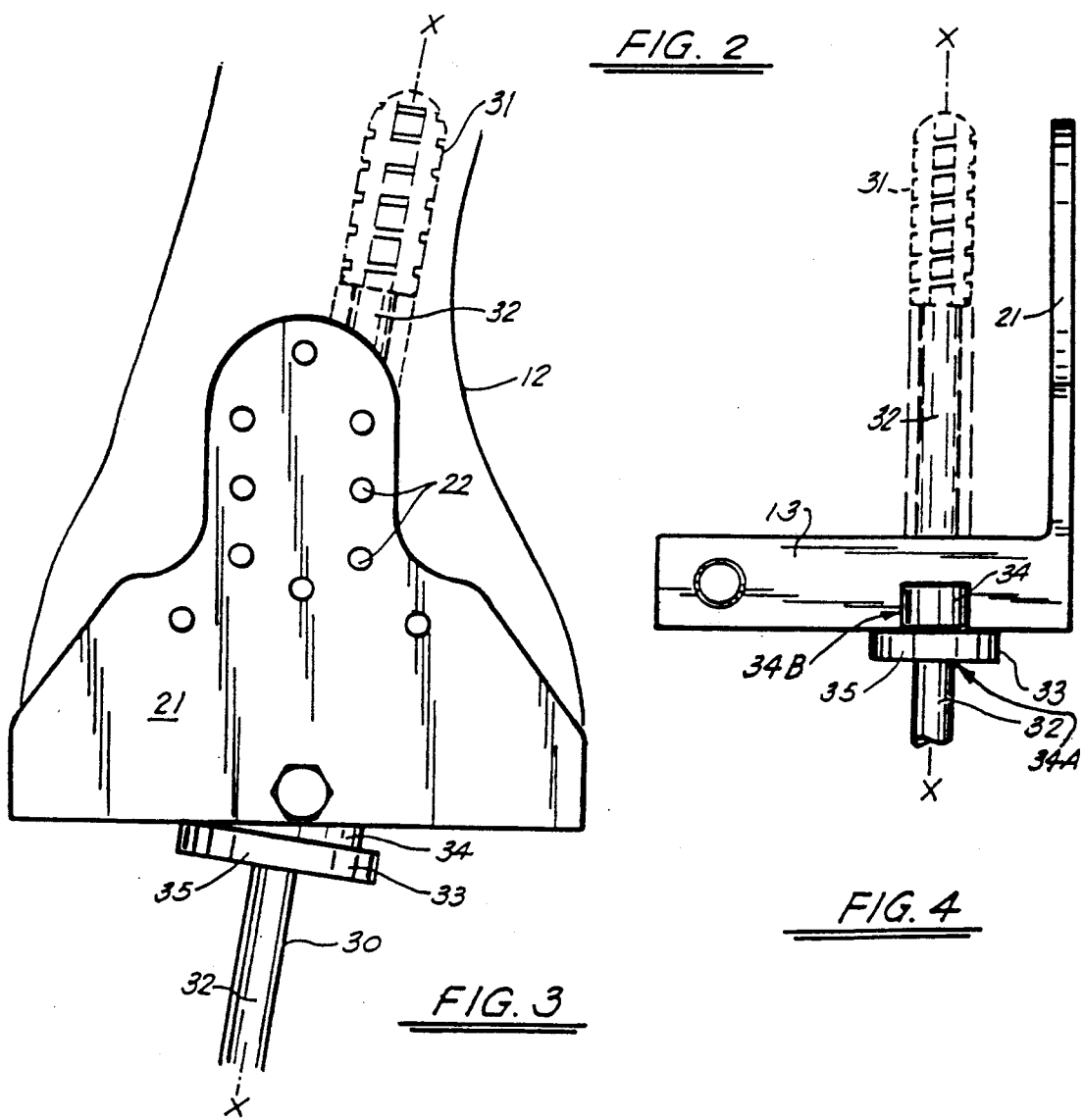

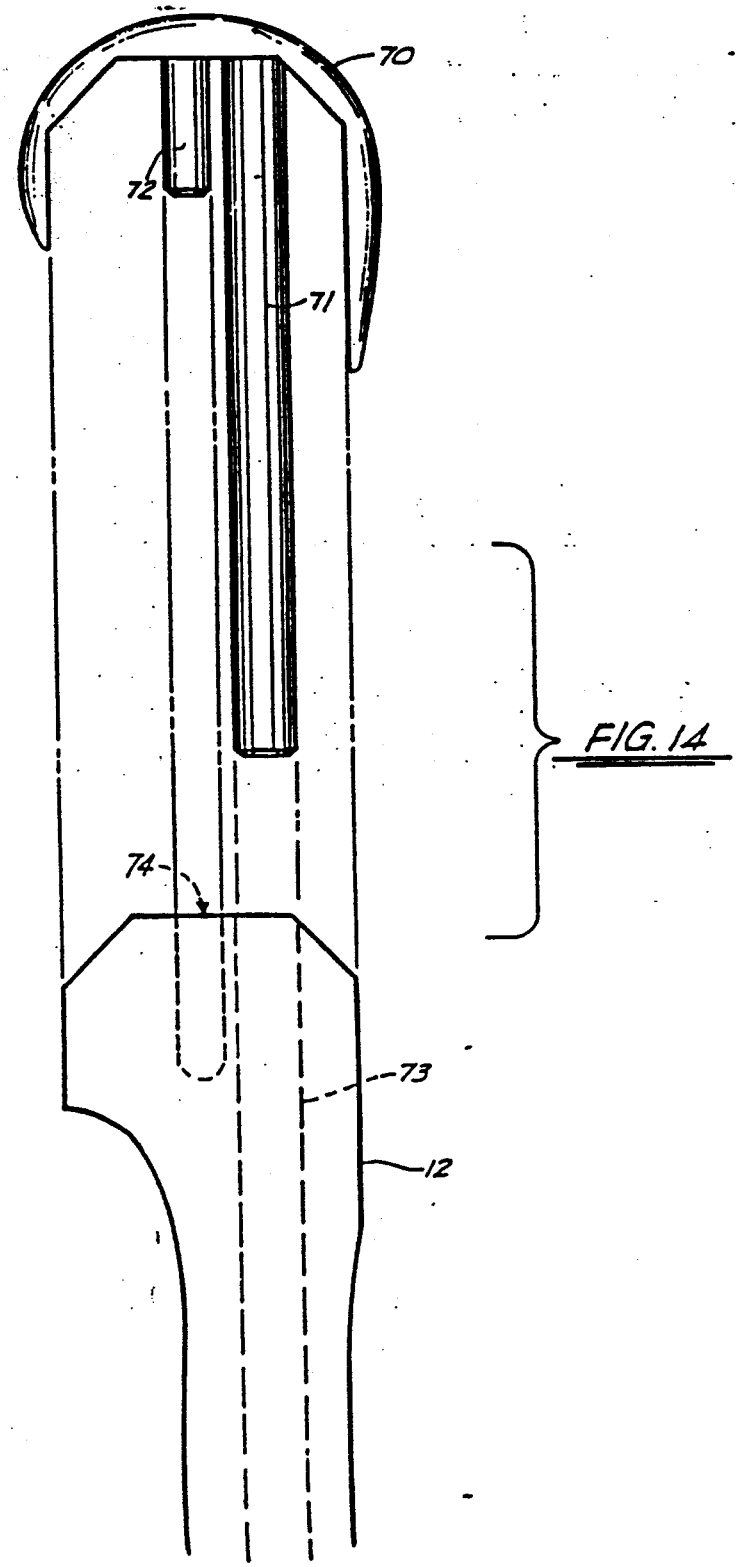

INSTRUMENTATION FOR LONG STEM SURGERY

CROSS REFERENCE TO RELATED APPLICATIONS

This is a continuation-in-part of copending U.S. patent application Ser. No. 07/765,379, filed Sep. 25, 1991, now U.S. Pat. No. 5,100,408, which is a continuation of U.S. patent application Ser. No. 053,037, both of which are hereby incorporated herein by reference.

BACKGROUND OF THE INVENTION

1. Field of the Invention

The present invention relates to improved tibial and femoral instrumentation method and apparatus for use in knee surgery and utilizing a plurality of reamers, each having a different cutting diameter to prepare a bore for the stem of a knee prosthesis and wherein the instrumentation registers upon a selected of the reamers that is of sufficient diameter particularly, the present invention relates to a system of knee surgery instrumentation that allows a surgeon to custom fit a knee prosthesis having a stem to a particular patient wherein the surgeon initiates a reaming of the intramedullary canal using a smallest cutting diameter reamer selected from a set of reamers, and progresses up in selected cutting diameters of the reamers until one of the reamers gets fixed or stuck in the patient's intramedullary canal, meeting resistance from cortical bone cutting or resecting instrumentation then registers upon the selected reamer after it cuts the cortical bone to prepare a bore for the prosthesis stem. All resectioning of the knee joint can be referenced to the reamer that is left in position when reaming is complete. The stem component of a knee prosthesis will closely fit the bore formed by the reamer. Instrumentation includes a cutting block oriented on the reamer, and all cuts made by the surgeon will be oriented relative to the stem or spike component of the prosthesis.

2. General Background

Often a knee prosthesis must be replaced, referred to as a revision case. In revision surgery, the existing component is removed from the tibia or femur. If cement was the means of attachment, it is cleaned and removed. The tibia or femur must then be recut.

Various devices have been patented which relate to the resectioning and preparation of the tibia or femur for prosthetic devices. In U.S. Pat. No. 4,474,177, entitled "Method and Apparatus For Shaping A Distal Femoral Surface", there is disclosed a method and apparatus for resectioning of the distal femur. An intramedullary reamer is used to internally locate the central longitudinal axis of the femur. The reamer is then removed and an intramedullary alignment guide is inserted in its place. The alignment guide has a handle attached to a rod portion at a preselected angle. Femoral surface modifying instruments can then be fixed to the guide handle and thus assume proper alignment with respect to the central longitudinal axis of the femur.

In U.S. Pat. No. 4,567,885, entitled "Triplanar Knee Resection System", there is provided a system for preparing a knee joint for a prosthesis. The triplanar system includes a guide member which has three pairs of parallel slots. The system further includes an intramedullary guide rod which is inserted into the femur. The guide rod has a 90° bend. The guide member is affixed to the guide rod, the guide rod being used as an alignment means for the guide member. This patent is a divisional of U.S. Pat. No. 4,487,203, issued Dec. 11, 1984.

U.S. Pat. No. 4,722,330, entitled "Femoral Surface Shaping Guide For Knee Implants", discloses a distal femoral surface shaping guide for mounting on an intramedullary alignment guide. The main body of the shaping guide preferably contains at least one shaping guide surface. It may have an attachment for other shaping surfaces, however, preferably the main body of the shaping guide has integrally formed shaping guide surfaces.

U.S. Pat. No. 4,791,919, entitled "Surgical Instruments", discloses a set of femoral instruments which includes a femoral intramedullary alignment rod which may be introduced into the medulla by an alignment rod introducer. An angle adaptor which slides over the alignment rod forms a basis for the preparation of the femur using saw guides to receive the femoral component of the knee prosthesis.

U.S. Pat. No. 4,703,751, entitled "Method And Apparatus For Resecting A Distal Femoral Surface". The '751 patent discloses a method and apparatus for resecting a distal femoral surface. The apparatus includes an intramedullary rod, a jig which attaches to the rod, a cutting plate and a reference bar. The method and apparatus disclosed are for forming the initial resection along the transverse axis.

U.S. Pat. No. 4,738,254, entitled "Positioner For Surgical Instruments", discloses a positioner for surgical instruments used to invade a bone. The positioner comprises a body means, an alignment plate, and an alignment rod. The body has at least one guide surface for positioning a resectioning surgical instrument. The alignment rod which extends into the femoral shaft is used to locate the main body of the femoral resection guide in the correct position.

In U.S. Pat. No. 4,759,350, there is disclosed an apparatus and system for preparing distal femur and proximal tibia ends to receive a knee prosthesis. An intramedullary alignment guide is used to reference a femoral alignment guide for attachment across the distal femur after the distal femur cut has been made. The femoral alignment guide is in turn a reference for several cutting guides.

U.S. Pat. No. 4,907,578, discloses a distal femoral resector for resecting the distal femur. The resector comprises a T-shaped base with a rotating rod mounted through the base and an intramedullary alignment rod. The resector has a guide slot for guiding a cutting tool.

U.S. Pat. No. 4,935,023, there is disclosed a distal femoral surface shaping guide which is mounted on an intramedullary alignment rod. The apparatus and method disclosed are particularly suitable for shaping one condyle for attachment of a unicondylar prosthesis.

SUMMARY OF THE INVENTION

The present invention provides an instrumentation system for long stem surgery. The present invention provides a number of reamers in a set, and cutting instrumentation mounts to a selected of the reamers after the selected size cuts a prepared bore for the knee prosthesis in cortical tissue. The instrumentation will be used in knee surgery where a knee prosthesis component has a stem that registers in a patient's tibia or femur.

Instruments are always correctly oriented as is the knee prosthesis, by making all cuts relative to a selected reamer after it has cut a prepared bore into the cortical bone tissue.

If the case is a revision surgery, the existing component is removed from the tibia or femur. If cement was the means of attachment, it is cleaned and removed.

The present invention thus provides an improved method and apparatus for implanting a knee prosthesis component having a stem that registers with a patient's leg bone intermedullary canal.

The method and apparatus of the present invention first uses a reamer selected from a group or set of reamers. Each of the reamers is of an increasingly larger external diameter. For example, the first reamer can be relatively small such as for example, having a cutting diameter of ten millimeters. Additional reamers can be in sizes up to for example twenty-two millimeters, and in one millimeter increments. The surgeon then is allowed to start with a small reamer such as the ten millimeter size and progress with increasingly larger external cutting diameter reamers to preliminarily ream the intermedullary canal of the patient's leg bone. By using progressively larger reamers to ream the patient's leg bone, a surgeon can insure that the smallest possible size reamer will be selected yet still cut into cortical bone sufficiently to define a prepared bore that will closely conform to and abut the stem of the selected knee prosthesis component during use. Thus for example, the surgeon can select a reamer that initially does not cut cortical bone three hundred and sixty degrees (360°). That particular reamer may be for example, twelve millimeters in diameter. However, if the surgeon continues to increase in size, it is possible that the fourteen millimeter cutting diameter reamer for example, might meet resistance and become initially stuck in the intermedullary canal so that the surgeon knows that three hundred and sixty degrees (360°) of cortical bone tissue is cut once reaming is completed.

After the surgeon prepares a bore by cutting three hundred and sixty degrees (360°) of cortical bone, a knee prosthesis is selected having a stem with the same external diameter as the cutting diameter of the selected reamer. Further, the surgeon can then correlate a cutting of the leg bone knee joint area to conform to the angle between the stem and the table of the knee prosthesis. Thus, cutting instrumentation is mounted upon the selected reamer as the reamer occupies the intermedullary canal and as the distal end portion or cutting end portion of the reamer fits against the prepared bore. In short, the surgeon simply leaves the reamer in position as soon as the prepared bore is cut. Thus, the reamer defines a reference axis for the cutting instrumentation installed thereon.

Once the cutting instrumentation is installed, the surgeon cuts the leg bone at the knee joint area using the cutting instrumentation supported by the selected reamer and externally of the intermedullary canal.

The upper portion of the reamer is preferably cylindrically shaped, defining a non-cutting end portion of the reamer that supports the instrumentation during cutting.

The plurality of reamers are of different cutting diameters, each having preferably a cylindrically shaped cutting end portion that conforms to the shape of the stem of the knee prosthesis.

The surgeon begins with a smaller reamer having a smaller diameter and inserts progressively larger reamers into the patient's intermedullary canal until a reamer is selected that is capable of reaming three hundred and sixty degrees (360°) of cortical bone tissue at the distal end of the reamer.

It is preferred that the reamers span a range of millimeters in size such as for example 10–22 millimeters in diameter, with the different reamers being spaced apart by one millimeter in diameter. Thus, the reamers will be supplied in cutting diameters of ten, eleven, twelve, thirteen, fourteen, fifteen, sixteen, seventeen, eighteen, nineteen, twenty, twenty-one, and twenty-two.

The cutting instrumentation can include a cutting block providing one or more flat cutting reference surfaces so that the cuts can be made by abutting a selected cutting reference surface with a cutting blade.

The present invention also provides a cutting instrumentation apparatus for use in preparing a knee joint area for a knee prosthesis. The apparatus includes a plurality of elongated rotary reamers, each having an upper proximal end portion and a lower distal end portion with a rotary cutting element thereon. In the set of reamers, each reamer is of a progressively larger cutting diameter.

An instrumentation assembly has a means for supporting the assembly during use upon a selected reamer at its upper end portion and externally of the patient's intermedullary canal.

The instrumentation assembly includes at least a cutting block with a cutting guide surface thereon for referencing a cutting blade so that selected bone tissue cuts can be made adjacent the knee joint area of the patient by aligning the cutting blade with the cutting guide surface.

The instrumentation system of the present invention also includes a drill guide for use with a selected of the reamers.

After the tibia or femur cut is completed, a correct size femoral drill guide is chosen by determining which guide fits best in the anterior/posterior and medial/lateral dimensions to ensure equal flexion and extension spaces. The femoral drill guide is positioned on the distal femur by placing the anterior ledge on the existing anterior femoral cortex.

Once correct medial/lateral and rotational orientation is achieved, the femoral drill guide is affixed to the femur anteriorly and/or medial/laterally by means of at least one pin or drill bit through the anterior ledge or through the attachable handle. The appropriate size femoral collet is attached to the femoral drill guide and positioned for a left or right knee.

The matching sized femoral reamer is then inserted through the femoral collet and is advanced into the intramedullary canal. The femoral reamer can be calibrated to determine how deep into the canal the reamer has advanced. Femoral lug holes can be drilled, if needed, through the femoral drill guide. When reaming and drilling is complete, the femoral drill guide is removed from the femur and the femoral reamer is left in place in the intramedullary canal.

The same size revision femoral anterior/posterior (A/P) cutting block is then attached to the intramedullary reamer. If the femoral lug holes have been drilled to accept the revision femoral A/P cutting block studs, the studs can then be placed into the holes for correct rotation orientation. If there is little or no femoral bone to affix the femoral anterior/posterior cutting block studs in, then the adaptable anterior femoral ledge can be attached to the cutting block. The correct rotation can be determined and the femoral anterior/posterior cutting block can be affixed to the anterior and/or medial/lateral femur by inserting at least one pin or drill bit through the adaptable anterior femoral ledge or the attachable handle. The anterior/posterior, and the anterior/posterior chamfer cuts can then be made through or over the femoral anterior/posterior cutting block.

If needed, the femoral drill guide can be reattached to the distal femur in the same manner as stated above and larger sized femoral collets can be positioned to ram for larger femoral stems.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 2 is a partial end view of the preferred embodiment of the apparatus of the present invention illustrating the femoral drill guide portion thereof with the collet attached;

FIG. 3 is a partial schematic anterior view of the preferred embodiment of the apparatus of the present invention illustrating the femoral drill guide portion with the reamer/drill in an operative position;

FIG. 4 is a partial side or lateral/medial view of the preferred embodiment of the apparatus of the present invention illustrating the drill guide portion with the reamer/drill in an operative position;

FIG. 14 is a schematic view of the distal femur after cutting and prior to the affixation of a long stemmed femoral component thereto;

DETAILED DESCRIPTION OF THE PREFERRED EMBODIMENT

Figure 1:
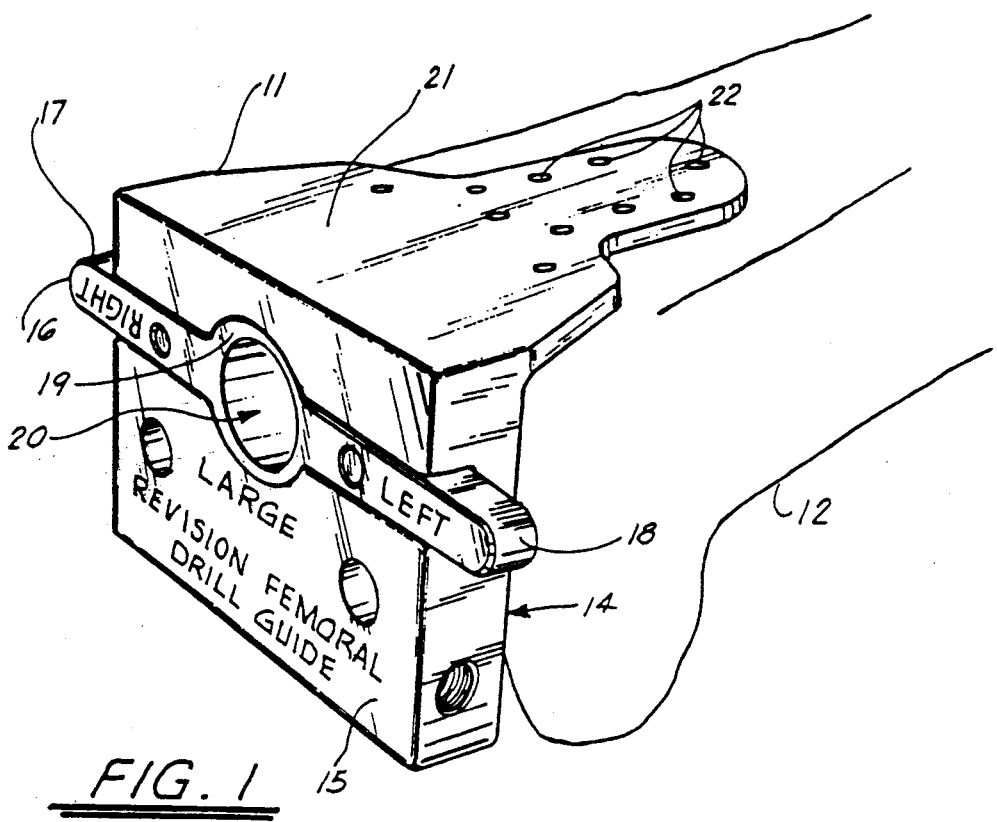
FIG. 1 is a partial perspective view of the preferred embodiment of the apparatus of the present invention illustrating the femoral drill guide portion thereof with collet attached.

The knee prosthesis surgical instrumentation apparatus 10 of the present invention includes a femoral drill guide body 11 (FIG. 1) adapted for placement during use on the distal femur 12. The drill guide 11 includes a generally rectangular portion 13 having a flat 14 under surface that orients upon the end of the distal femur 12A and a flat top surface 15 portion that accommodates removable collet 16. Collet 16 includes a pair of spaced apart handles 17,18 and a central portion 19 having a cylindrical opening 20 therethrough which is angularly oriented with respect to flat surfaces 14, 15. This angular orientation of opening 20 accommodates for the difference between the anatomical axis of the femoral intramedullary canal 12B and the mechanical axis which is defined by a line that passes through the center of the femoral head and the midline of the knee joint and ankle joint. The end of the distal femur is designated by the numeral 12A in FIG. 13.

In FIGS. 2 and 3, the drill guide 11 is shown in an end view and in a anterior view respectively upon femur 12. In FIG. 2, the posterior condyles 12C of the femur 12 can e shown extending beyond the bottom rectangular drill guide body 13. Removable collet 16 attaches to guide body 11 at an elongated slot 25 that extends transversely across the rectangular 13 portion of guide body 11. Slot 25 is shaped to receive collet 16. A pair of attachment posts 26, 27 receive collet 16 thereon. Collet 16 includes openings 28, 29 that register upon posts 26, 27. The posts 26, 27 can each be provided with a spring locking detent, such as a spring loaded ball, for example, to frictionally engage the collet 16 at the openings 28, 29.

An anterior ledge 21 provides a plurality of openings 22 that define drill or pin openings for preventing rotational and translational movement of the drill guide 11 with respect to femur 12. The anterior ledge 21 preferably provides a plurality of, for example, ten (10) openings 22 as shown in FIGS. 1 and 3. The surgeon can select any particular opening 22 for the placement of a pin or drill therethrough into the underlying femur for purposes of rigidifying the drill guide 11 and preventing rotation and translation.

In FIGS. 3-4, there can be seen an elongated drill/reamer 30 having a lower cutting 31 portion and a smaller diameter shaft 32 portion, a drill/reamer sleeve 33 manufactured of plastic, for example, provides an inside diameter cylindrical portion 34A and an outside diameter cylindrical portion 34B, and a larger diameter cylindrical portion 35 in the form of an enlarged collar. The inside cylindrical portion 34A is sized to accept and centralize the drill/reamer shaft diameter 32. The cylindrical portion 34 is sized to snugly fit and centralize in opening 20 of collet 16, as shown in FIGS. 3 and 4. The axis X—X of drill/reamer 30 is shown in FIG. 3 as being angled with respect to a line normal to the flat upper surface 15 and the flat under surface 14 of drill guide portion 13. The flat surfaces 14, 15 are preferably flat plane, and/or parallel to one another.

In the preferred embodiment, the angle formed by the drill/reamer 30 with respect to a line normal to surfaces 14, 15 is on the order of zero-twenty degrees (0°-20°) but preferably five-eleven degrees (5°-11°) which accommodates the large majority of anatomical situations. The collets 16 are removable and thus each collet provides an opening 20 having a different angular orientation. Further, the collets can be provided with openings 20 of different cylindrical diameter such as 8 millimeters, 9 millimeters, etc. Thus, the removable collets 16 provide an adjustability both with regard to the angle of orientation of the drill/reamer 30 and also with regard to the diameter of drills/reamers that can be used based upon the selection of the diameter of opening 20 and of the size of sleeve 33.

The collet 16 are preferably reversible, as shown in FIGS. 1 and 2, having left and right sides for accommodating left and right femurs. The surgeon simply selects the proper collet position so as to orient the opening 20 in the direction that will correctly track the intramedullary canal with the reamer/drill 30.

The drill guide 11 main rectangular body 13 has a pair of openings 36, 37 which are sized based upon the anchoring pins of the femoral knee component and located with respect to the long stem of the femoral component.

Figures 5, 6, 7:
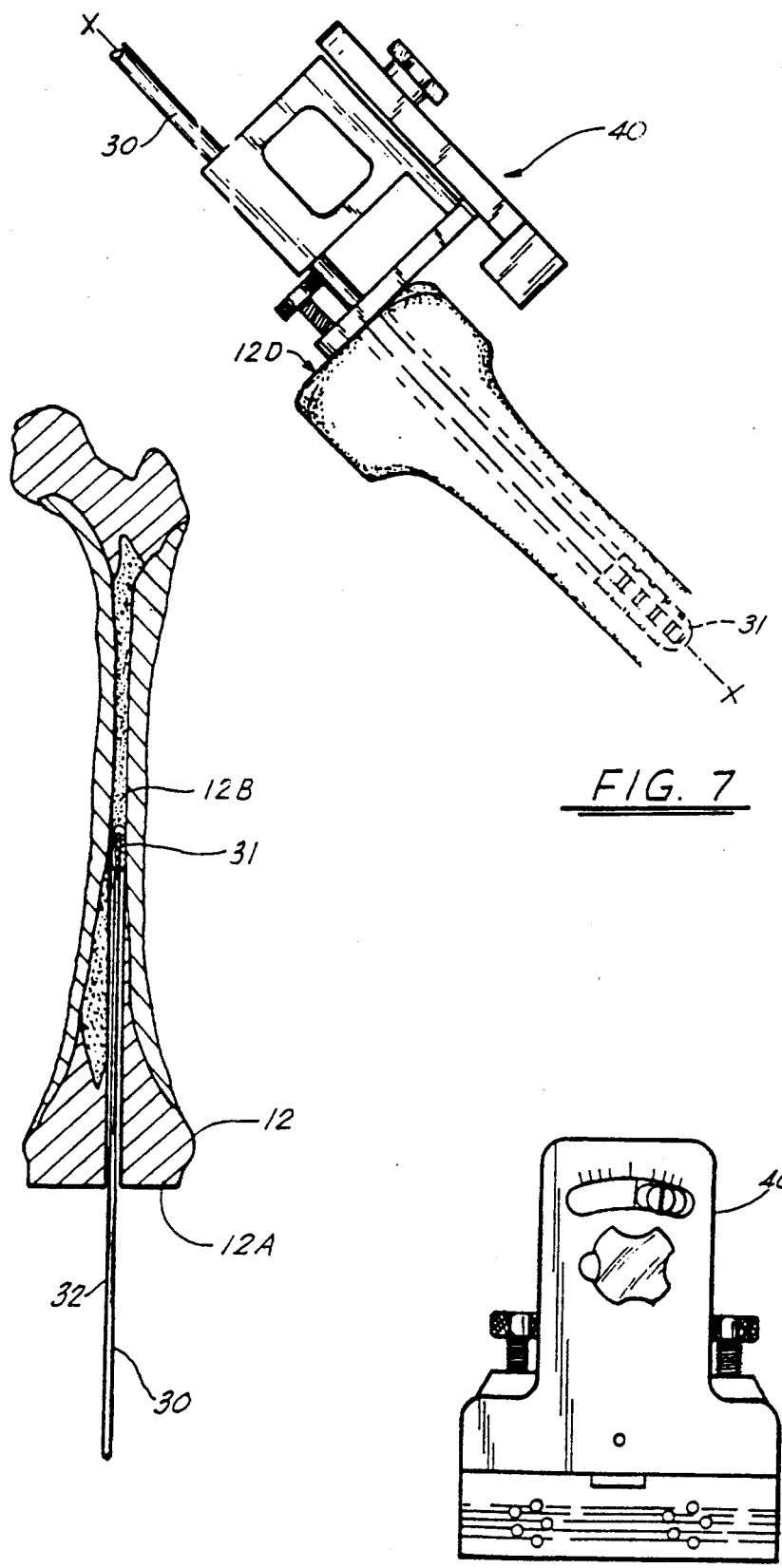
FIG. 5 is a partial side, schematic view of the preferred embodiment of the apparatus of the present invention illustrating the reamer/drill in an installed operative position within the intramedullary canal.
FIG. 6 is a top view of an alignment assembly/cutting block that can be used with the method of the present invention.
FIG. 7 is a side view or lateral/medial view of an alignment assembly/cutting block as aligned upon the drill/reamer as part of the method of the present invention.

FIGS. 5-10 illustrate the use of the femoral drill/reamer to orient a commercially available alignment guide. In FIG. 5, the femur 12 is illustrated with the flat distal end 12A in a revision case being shown. The drill/reamer 30 has been installed with the cutting 31 portion penetrating the intramedullary canal 12B. At this point, the drill/reamer 30 provides orientation for the alignment guide designated generally by the numeral 40 and thereafter, for the cutting block 50 portion of the present invention (see FIGS. 11-13).

Figure 8:
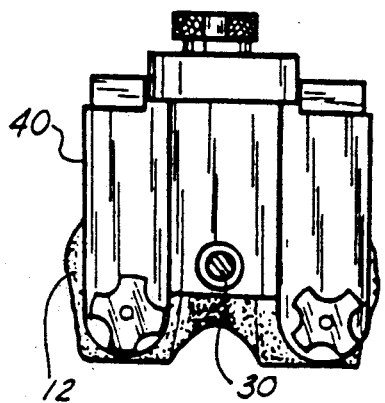
FIG. 8 is a end view of an alignment assembly/cutting block as aligned upon the drill/reamer as part of the method of the present invention.
Figure 9:
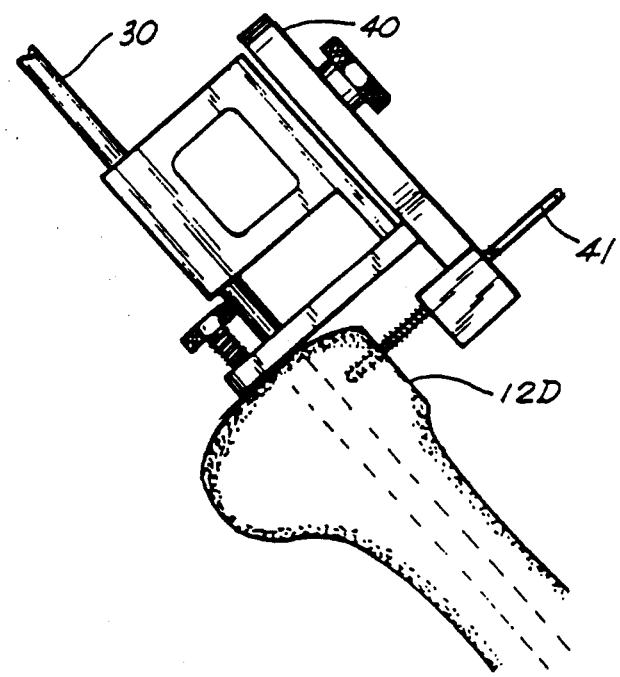
FIG. 9 is a side view of an alignment assembly/cutting block as aligned upon the drill/reamer as part of the method of the present invention.

FIG. 6 shows a top view of the alignment guide, whereas in FIG. 7, a side view is shown with the alignment guide positioned upon the drill/reamer and the top 12A of the distal femur. In FIG. 8 and 9, the proper orientation of the alignment guide 40 with femur 12 is shown, and upon drill/reamer 30 whereas FIG. 9 illustrates a side view thereof. A drill or pin 41 is illustrated in FIG. 9 as entering the anterior femur surface 12B.

Figure 10:
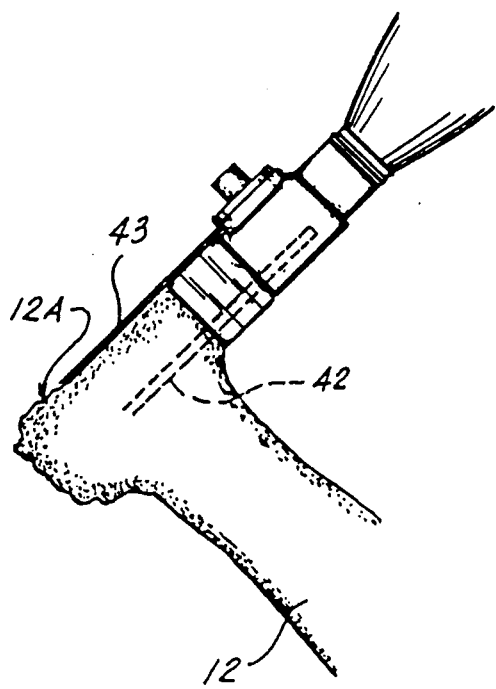
FIG. 10 is a side view or lateral/medial view of the femur illustrating a cutting of the distal femur as part of the method of the present invention.

The opening 42 formed by drill or pin 41 is shown in FIG. 10 wherein a blade 43 is used to dress the end of the distal femur 12A before attachment of the cutting block 50 thereto. It should be understood that the alignment guide illustrated in FIGS. 6-10 is a commercially available device sold by Smith & Nephew Richards Inc. of Memphis, Tenn. The alignment guide 40 is shown simply to illustrate how the drill/reamer 30 is used for orientation of the alignment guide 40 and also the cutting block 50 thereon after the drill/reamer 30 is installed using the femoral drill guide 11.

Figure 13:
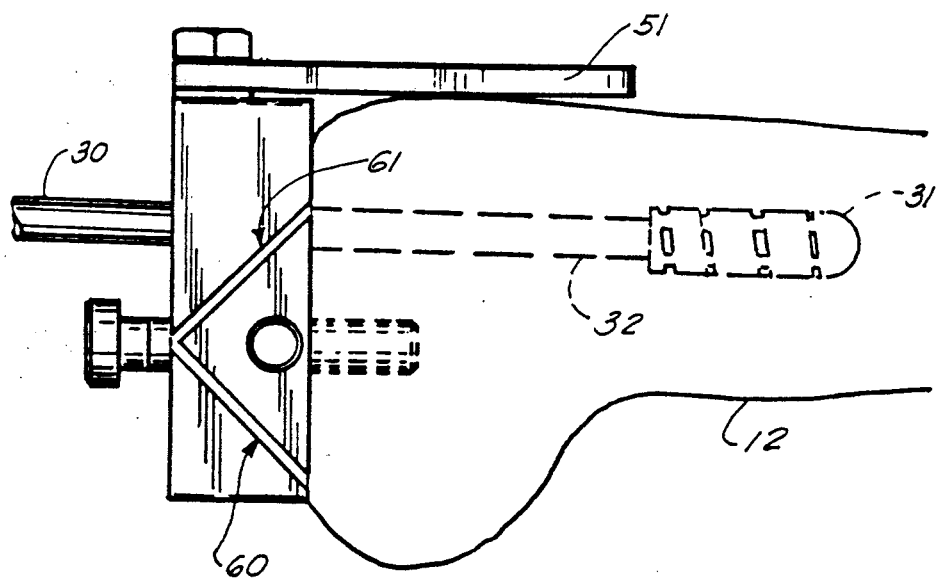
FIG. 13 is another partial side view of the preferred embodiment of the apparatus of the present invention illustrating the medial/lateral distal femur with revision anterior/posterior cutting block and anterior ledge adapter portions attached to the drill/reamer.
Figure 11:
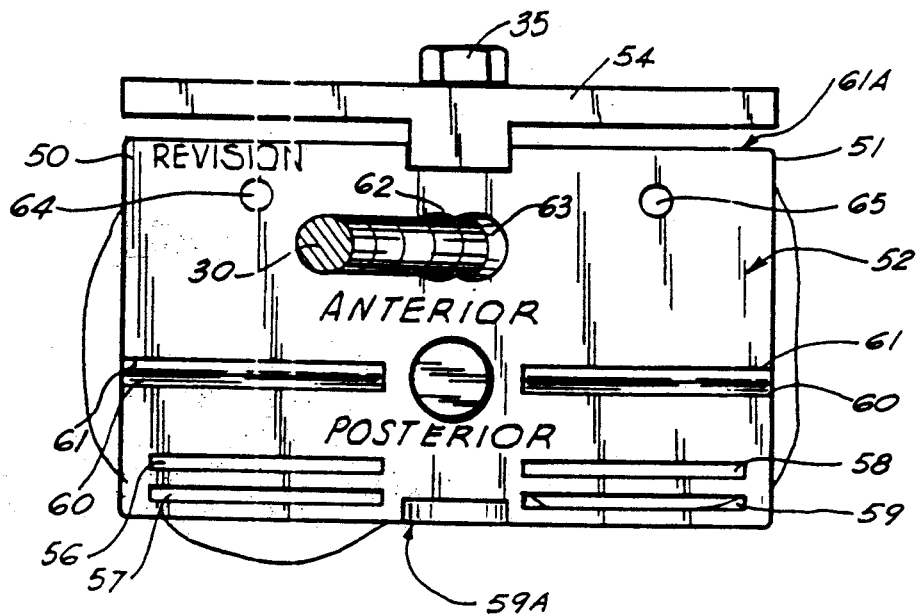
FIG. 11 is a partial end view of the preferred embodiment of the apparatus of the present invention illustrating the distal femur with revision anterior/posterior cutting block portion attached to the drill/reamer.
Figure 12:
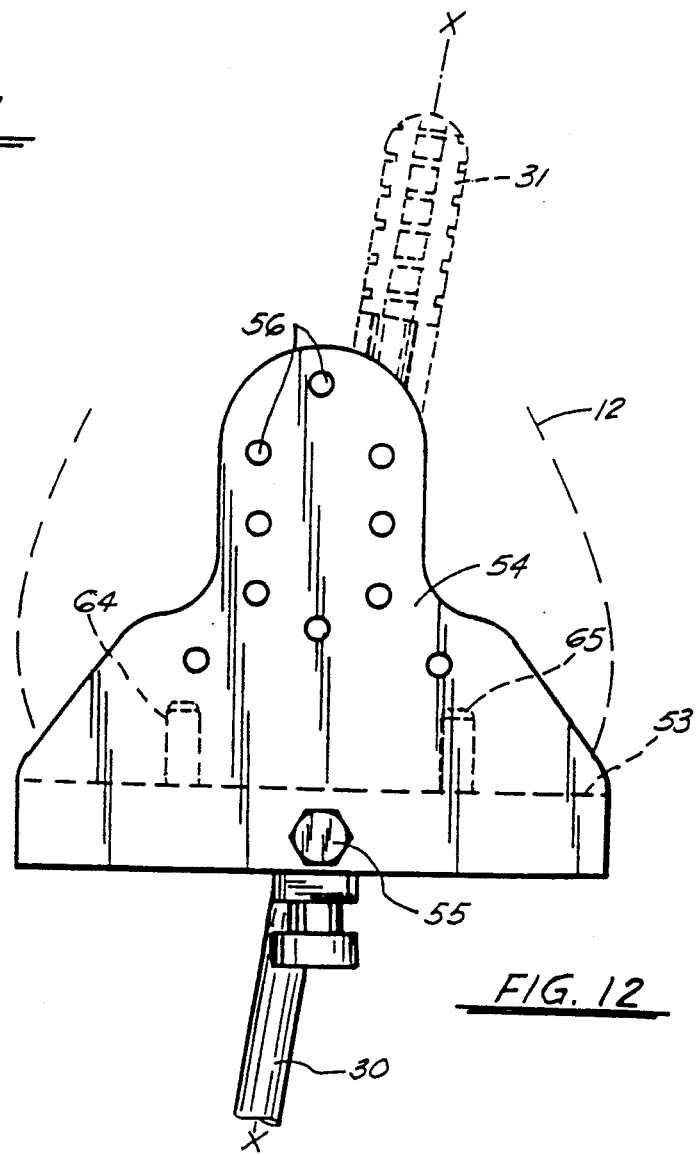
FIG. 12 is a partial view of the preferred embodiment of the apparatus of the present invention illustrating the anterior distal femur with revision anterior/posterior cutting block and anterior ledge adapter portions attached to the drill/reamer.

In FIGS. 11-13, the revision femoral anterior/posterior cutting block 50 is shown, comprising a generally rectangular cutting block portion 51 having an upper generally flat surface 52 and a lower flat surface 53 with an anterior ledge 54 being removably attached at bolted connection 55. The anterior ledge 54 can be shaped correspondingly to the ledge 21 of femoral drill guide 11, having the same plurality of openings to accommodate a drill or pin as the openings 22 of anterior ledge 21. Thus, the plurality of openings 56 in anterior ledge 54 can be correspondingly placed to the plurality of openings 22 in anterior ledge 21 of drill guide 11.

The cutting block 50 provides a plurality of guide slots 56-59 and guide surface 59A which are parallel and which accommodate a cutting blade for making posterior femoral cuts. The guide surface 61A accommodates a cutting blade to make the anterior femoral cut. A plurality of diagonal slots 60, 61 (FIG. 13) are provided for making diagonal cuts to the distal end of femur 12 when the cutting block 50 is positioned, as shown in FIG. 13. The cutting block 50 is preferably provided with a pair of permanent angled openings 62, 63, (or openings carried in collets) each of which is angled by a measure equal to the anatomical offset of the intramedullary canal as defined by the position of the drill/reamer 30 when occupying the intramedullary canal of the femur. The surgeon simply selects the degree of orientation of the cutting block 50 for a given anatomical offset by selecting from a plurality of cutting blocks 50, or by means of removable collets. The cutting block 50 can provide a pair of spaced apart pegs 64, 65 that register in cavities 74 that were made through openings 36, 37 of femoral drill guide 11 or left in the distal femur by the previous femoral component for the knee prosthesis.

In FIG. 14, the femur 12 is illustrated with the cuts having been made using cutting block 50 and prior to the installation of a new long stem component 70 that includes an elongated stem 71 and a pair of spaced apart pegs 72, the stem 71 registering in the opening 73 that has been formed in the intramedullary canal using drill/reamer 30. The pair of cavities 74 represents openings in the femur 12 for accommodating the pair of pegs 72.

FIGS. 15-19 illustrate the method of the present invention for implanting knee prosthesis component 70 having stem 71 that registers with the patient's tibia 75 and more particularly the intramedullary canal 78 portion as more fully described hereinafter.

The method of the present invention first requires the placement of a selected reamer/drill 30 which is selected from a group of reamers 30. Each of the reamers if of an increasingly larger external cutting diameter and is used to preliminarily ream the intramedullary canal 78 of the patient's tibia 75 and to a desired depth and internal diameter which corresponds to the length and external diameter of the stem 71 of a knee prosthesis component 70. Typically, the reamers 30 would be provided in a range of diameters beginning for example at ten (10) millimeters in cutting diameter and up to for example twenty-two millimeters in cutting diameter and one millimeter apart in diameter from one reamer 30 to the next, for example.

The surgeon begins the method of the present invention by selecting the smallest diameter reamer 30 that is provided in the set of reamers ten through twenty-two (10-22) millimeters in cutting diameter, for example. The surgeon then progresses up by inserting one reamer 30 at a time into the intramedullary canal 78 until the surgeon finds a reamer 30 that is large enough to get fixed or stuck in the intermedullary canal 78 at a selected stem length.

By progressing upwardly in reamer 30 cutting diameters, the surgeon is assured of eventually selecting a reamer having sufficiently large diameter that it becomes fixed or stuck in the intermedullary canal 78 at a desired depth as calibrated on the reamer itself, for example.

It is desirable that the reamer 30 be selected of sufficiently large external cutting diameter that the reamer 30 distal end portion 31 is cutting cortical bone to define a prepared bore that will abut and conform to the stem 71 of the knee prosthesis component 70 upon installation of the component 70.

The surgeon simply inserts each progressively larger reamer 30 into the intermedullary canal 78 of the patient's tibia 75 beginning at the proximal tibia 76 and extending down into the distal tibia 77 until the length of the stem 71 is reamed three hundred and sixty degrees (360°) of cortical bone to accommodate the stem 70.

Figure 15:
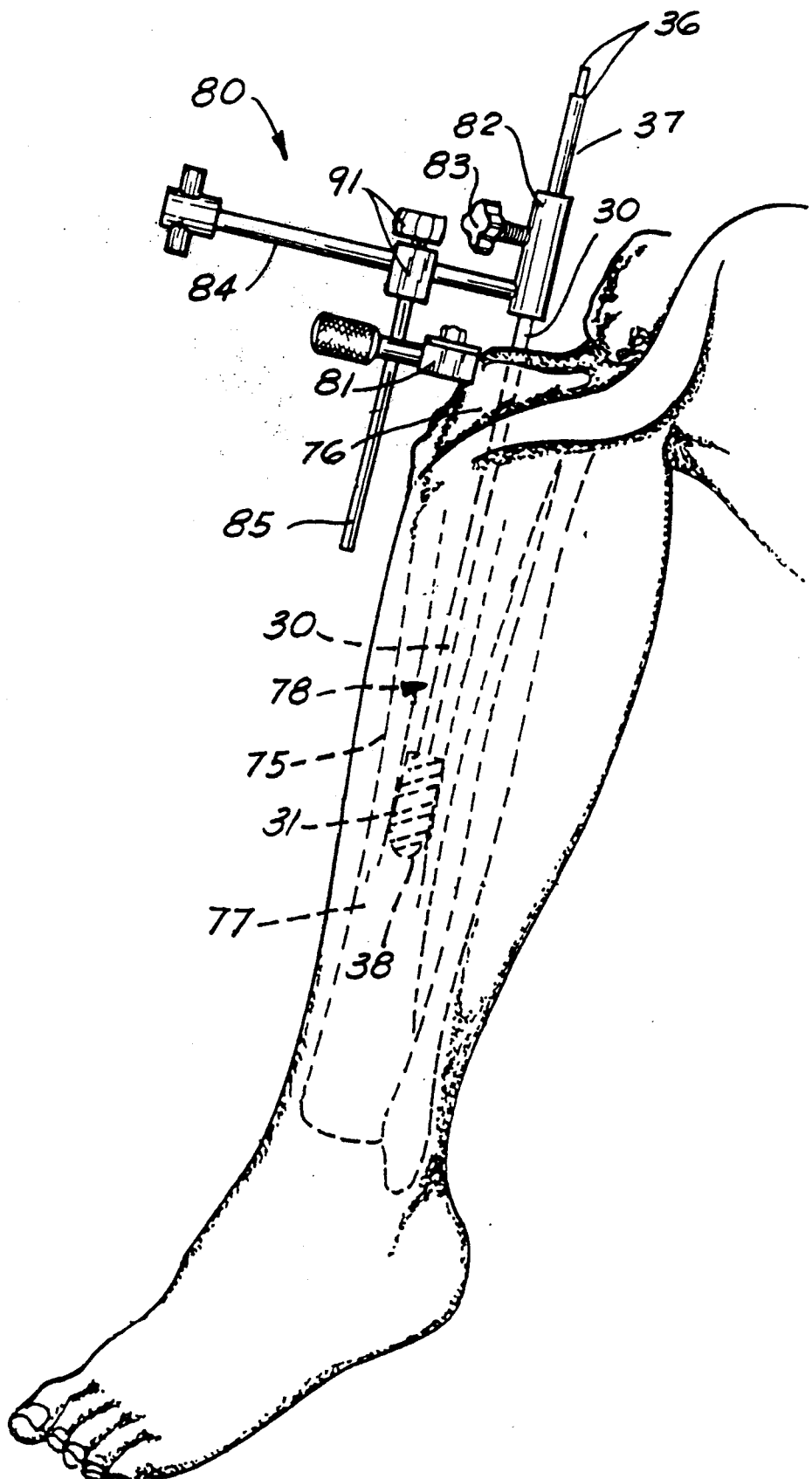
FIG. 15 is a schematic view illustrating the method of the present invention wherein the intermedullary canal is reamed with a reamer of selected cutting diameter.
Figure 17:
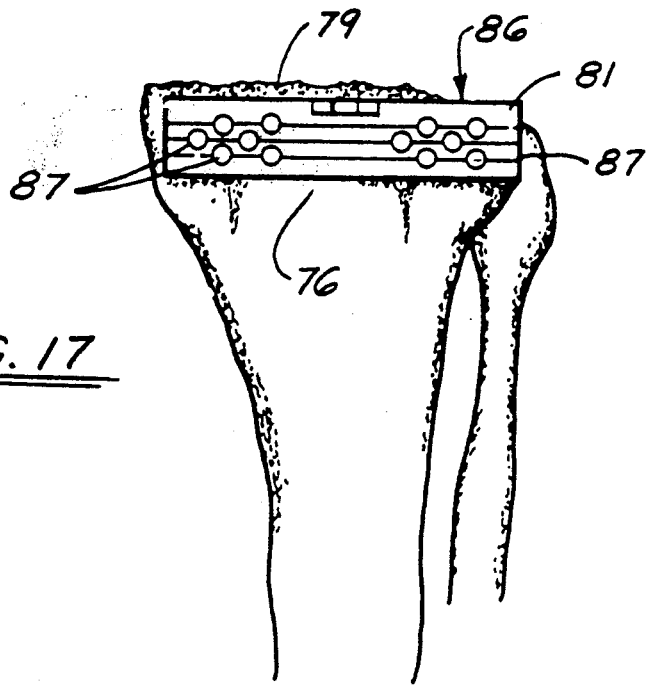
FIG. 17 is a schematic anterior view illustrating placement of a cutting block portion of the instrumentation as referenced to the reamer.
Figure 16:
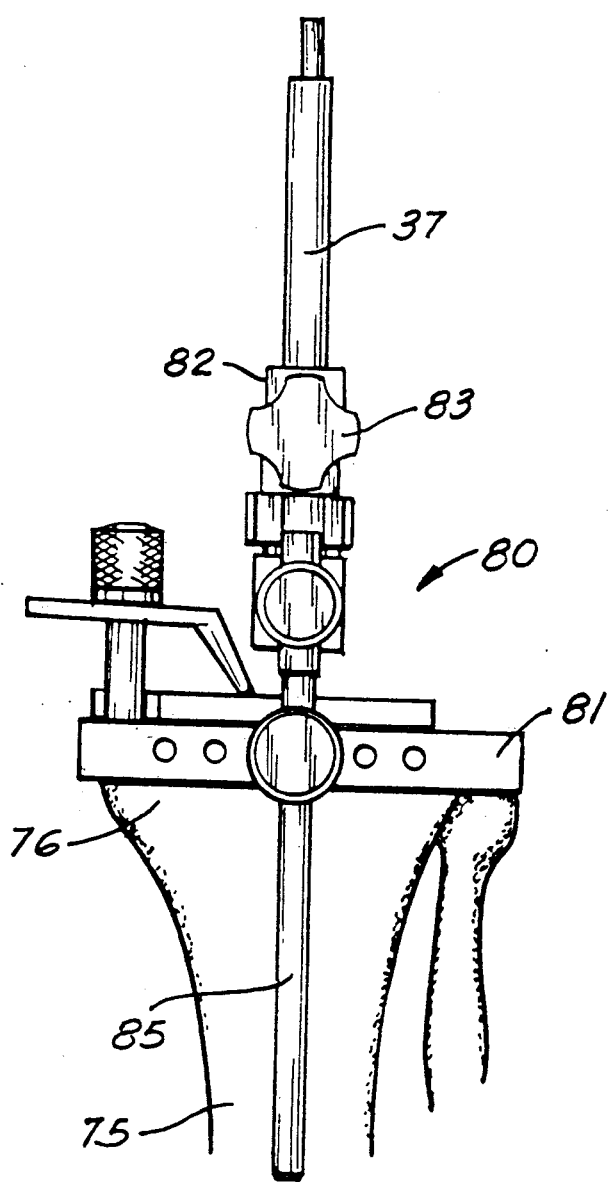
FIG. 16 is a schematic illustration of the method of the present invention illustrating an interior view of the instrumentation as installed upon the reamer.

When the selected reamer 30 has been used to cut cortical bone a distance equal to the length of the stem 71 of the knee prosthesis component 70, the surgeon installs instrumentation and alignment assembly 80. Instrumentation and alignment assembly 80 provides a tibial cutting block 81 that is adjustably supported as shown in FIGS. 15-17 adjacent the proximal tibia 76. This allos the tibial condylar surface 79 to be cut and prepared with a flat or shaped surface that corresponds to the flat underside shape of the knee prosthesis component 70.

Tibial cutting block 81 is supported upon the generally vertically extending rod 85 portion of instrumentation assembly 80 and can be adjustable upwardly or downwardly and fixed in a desired position thereupon with a clamp (not shown). This affixes the cutting block 81 with respect to generally vertically extending rod 85.

The entire instrumentation assembly 80 is mounted directly upon the upper end 36 portion of drill/reamer 30 and more particularly upon the cylindrically shaped upper end 37 thereof. This allows a desired adjustment of cylindrical bushing 82 with respect to cylindrical upper end 37 of drill/reamer 30. A set screw 83 can be provided for affixing the position of bushing 82 and thus instrumentation assembly 80 in a desired elevational position with respect to the drill/reamer 30. Bushing 82 carries a horizontally extending rod 84 upon which vertically extending rod 85 is attached at clamp 91. Thus, the position of cutting block 81 can be adjusted in a proximal/distal direction as well as in an anterior/posterior direction.

Cutting block 81 provides a flat upper surface 86 that can be used to register a cutting blade 91 thereupon as shown in FIG. 4. The surgeon can use a flat cutting blade 91 portion of bone cutting instrument 90 (commercially available) to resection the patient's tibial condylar surface 79 so that the surface 79 provides a flat surface receptive of the flat underside of tibial component 70.

Figure 18:
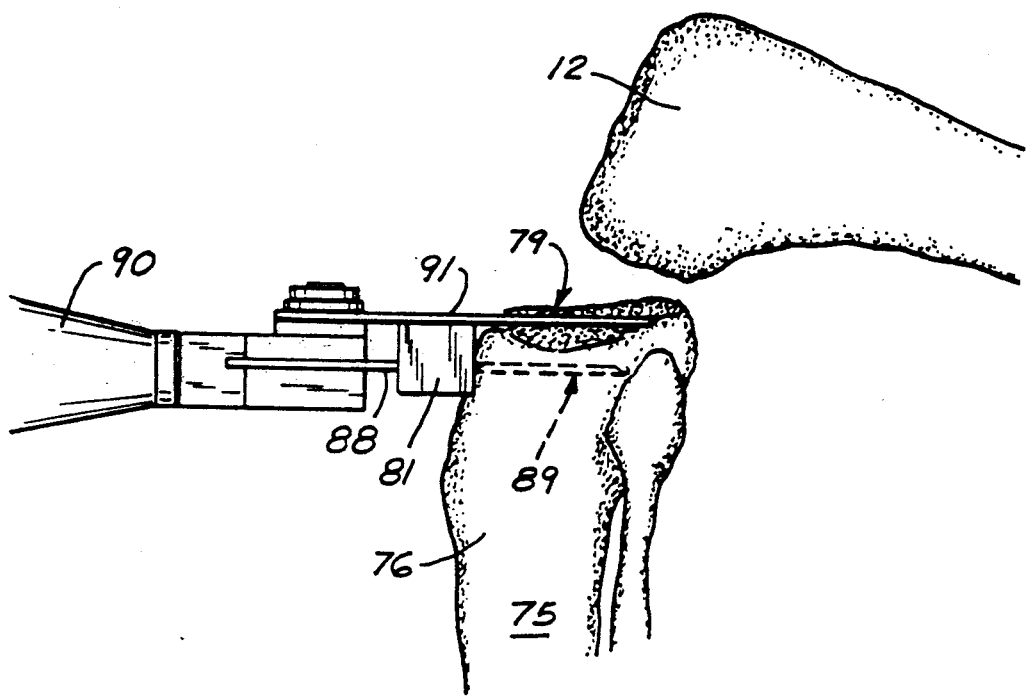
FIG. 18 illustrates use of the cutting block for cutting the bone tissue adjacent the knee joints.
Figure 19:
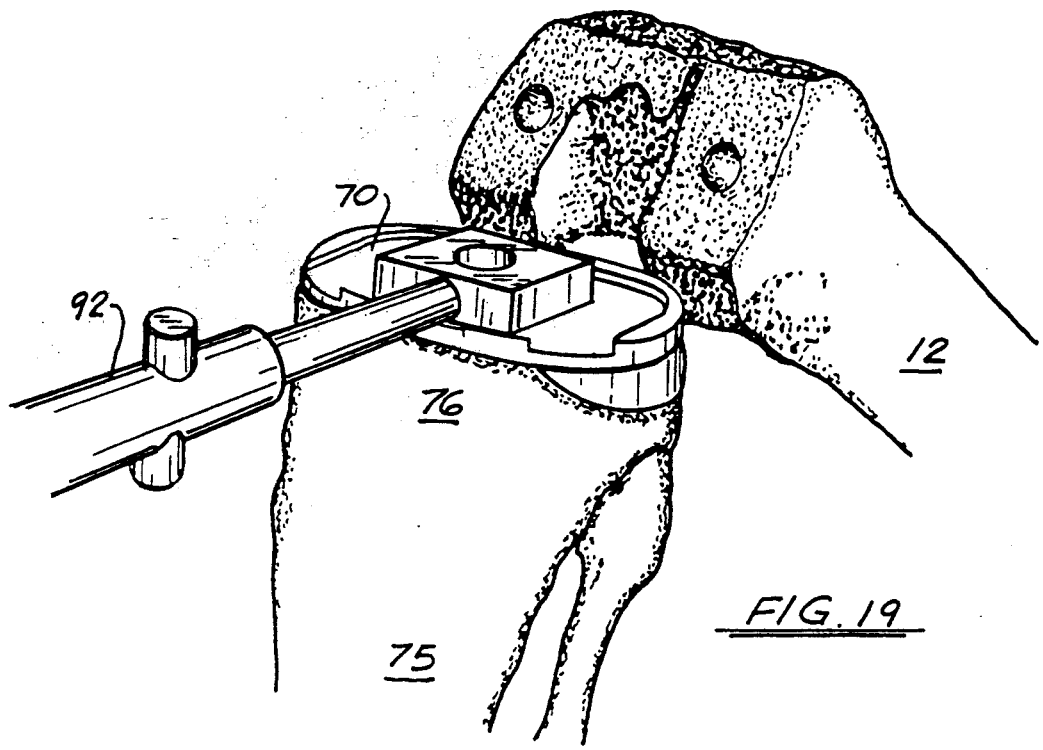
FIG. 19 is a perspective view illustrating placement of the knee prosthesis component after reaming of the intermedullary canal to accept the prosthesis stem, and after resectioning of the bone tissue adjacent the knee joint.

In practice, the cutting block 81 is moved to a desired position so that the upper flat surface 86 is in a desired orientation with respect to the patient's tibial condylar surface 79. The surgeon then places pins 88 through openings 87 in the cutting block 81 as shown in FIGS. 17 and 18. Drills or pins 88 are placed through openings 87 and into the underlying bone tissue and into formed openings 89. This affixes the position of block 81 with respect to the patient's tibial condylar surface 79. The surgeon then simply places the cutting blade 91 upon the flat upper surface 86 of cutting block 81. In this fashion, the proximal tibia 76 can be cut as desired to exactly conform to the bottom of prosthesis 70. In FIG. 19, an instrument 92 (commercially available) is shown after placement of the knee prosthesis component 70 into the patient's tibia 75.

Thus the present invention provides a method for implanting a knee prosthesis component having a stem that registers with the patient's tibial intermedullary canal and wherein the reamer is used as a reference for resecting the proximal tibia. This insures that the knee prosthesis component will fit flush on the proximal tibia because the instrumentation used to resect the proximal tibia is referenced directly to the reamer and the reamed hole exactly conforms to the stem 71 of the prosthesis 70.

| Part Number | PARTS LIST Description |
|---|---|
| 10 | knee prosthesis instrumentation |
| 11 | guide body |
| 12 | femur |
| 12A | distal femur |
| 12B | anterior condylar surface |
| 12C | posterior condylar surface |
| 13 | rectangular portion |
| 14 | flat undersurface |
| 15 | flat top surface |
| 16 | collet |
| 17 | handle |
| 18 | handle |
| 19 | central portion |
| 20 | opening |
| 21 | anterior ledge |
| 22 | openings |
| 25 | slot |
| 26 | attachment post |
| 27 | attachment post |
| 28 | opening |
| 29 | opening |
| 30 | drill/reamer |
| 31 | cutting portion |
| 32 | shaft portion |
| 33 | sleeve |
| 34A | inside diameter portion |
| 34B | outside diameter portion |
| 35 | cylindrical portion |
| 36 | upper end drill/reamer |
| 37 | cylindrical upper end |
| 38 | hemispherical tip |
| 40 | alignment guide |
| 41 | drill/pin |
| 42 | opening |
| 43 | blade |
| 50 | cutting block |
| 51 | cutting block portion |
| 52 | flat surface |
| 53 | flat surface |
| 54 | anterior ledge |
| 55 | bolted connection |
| 56 | slot |
| 57 | slot |
| 58 | slot |
| 59 | slot |
| 59A | slot surface |
| 60 | diagonal slot |
| 61 | diagonal slot |
| 62 | angled opening |
| 63 | angled opening |
| 64 | peg |
| 65 | peg |
| 70 | knee prosthesis component |
| 71 | stem |
| 72 | peg |
| 73 | opening |

| Part Number | Description |
| --- | --- |
| 74 | cavity |
| 75 | patient's tibia |
| 76 | proximal tibia |
| 77 | distal tibia |
| 78 | intramedullary canal |
| 79 | tibial condylar surface |
| 80 | instrumentation assembly |
| 81 | tibial cutting block |
| 82 | cylindrical bushing |
| 83 | set screw |
| 84 | horizontal rod |
| 85 | vertical rod |
| 86 | flat upper surface |
| 87 | openings |
| 88 | pin |
| 89 | opening in bone |
| 90 | bone cutting instrument |
| 91 | blade |
| 92 | instrument |
| 93 | clamp |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A method of implanting a knee prosthesis component having a stem that registers with the patient's leg bone intramedullary canal comprising the steps of:
   a) using a rotary reamer of a first smaller diameter with a distal end portion having a cutting portion that defines a cutting diameter during use, the reamer being selected from a group of reamers, each of an increasingly larger external diameter to preliminarily ream the intramedullary canal of a patient's leg bone to a preselected diameter, and beginning at the knee joint area;
   b) using progressively larger diameter reamers to ream the intramedullary canal of the patient's leg bone until a reamer is selected that has a sufficiently large external cutting diameter that the reamer distal end portion is cutting cortical bone to define a prepared bore that will abut the stem of the selected knee prosthesis component during use;
   c) installing cutting instrumentation on the selected reamer as the reamer occupies the intramedullary canal and the distal end portion fits against the bore, wherein the reamer defines a reference axis for the cutting instrumentation;
   d) cutting the leg bone at the knee joint area using the cutting instrumentation supported by the selected reamer; and
   e) placing the stem of a selected knee prosthesis component in the patient's intramedullary canal wherein the stem fits the prepared bore.

2. The method of claim 1 wherein the reamer is step "d" has a lower distal cutting end portion positioned in the intramedullary canal at the bore and an upper, non-cutting end portion that supports the instrumentation.

3. The method of claim 1 wherein a plurality of reamers of different diameters are sequentially placed in the intramedullary canal beginning with a small reamer having a smaller diameter and inserting progressively larger reamers until a reamer is selected that is capable of reaming three hundred sixty degrees (360°) of cortical bone tissue at the distal end of the reamer.

4. The method of claim 3 wherein the smallest diameter reamer is ten (10) millimeters or less in diameter.

5. The method of claim 1 wherein in step "a" the reamer has upper and lower end portions, and the lower end of the reamer extends into the intramedullary canal, and the upper end portion remains exposed and externally of the intramedullary canal.

6. The method of claim 1 wherein in step "c" the cutting instrumentation provides one or more flat cutting reference surfaces and in step "d", cuts are made by abutting a selected reference surface with a cutting blade.

7. The method of claim 1 wherein in step "d", the reamer is advanced sufficiently into the intramedullary canal to create a rotational frictional resistance between the reamer and the cortical bone tissue during reaming.

8. The method of claim 1 wherein in step "b" the cutting instrumentation is supported upon the reamer at spaced apart locations.

9. The method of claim 1 wherein a smaller of the reamers is of a cutting diameter of ten (10) millimeters.

10. A cutting instrumentation system for use in preparing a patient's bone tissue at the patient's knee joint area for a knee prosthesis, and wherein the bone tissue has a proximal bone tissue surface that is generally transverse to the patient's intramedullary canal, comprising;
    a) a plurality of elongated rotary reamers, each having an upper proximal end portion and a lower distal end portion having a rotary cutting element thereon, wherein each respective reamer has a rotary cutting element of a progressively larger cutting diameter;
    b) an instrumentation assembly having means thereon for supporting the assembly during use upon a selected reamer at its upper end portion and in a position externally of the patient's intramedullary canal so that the instrumentation assembly is referenced upon the reamer; and
    c) the instrumentation assembly with an opening that closely fits the reamer to fix the angle of the cutting block relative to the reamer, the cutting block surrounding the reamer during use and providing a surface portion including a cutting block that closely fits the patient's proximal bone tissue surface at the knee joint area;
    d) the block having a cutting guide surface thereon for referencing a cutting blade so that selected bone tissue cuts can be made adjacent the knee joint area of the patient.

11. The cutting instrumentation of claim 10 wherein the cutting guide surfaces are generally flat.

12. The cutting instrumentation of claim 10 further comprising a prosthesis having a stem and a transverse table attached to the upper end of the stem defining an angle therewith, and wherein the cutting block has a flat planar cutting guide surface that intersects the reamer linear axis at said angle.

13. The cutting instrumentation of claim 12 wherein the stem is of a generally uniform cylindrically-shaped cross section.

14. The cutting instrumentation of claim 10 wherein said plurality of elongated reamers include a smaller reamer having a cutting diameter of about ten (10) millimeters, and a plurality of larger cutting diameter reamers.

15. The cutting instrumentation of claim 14 wherein the plurality of reamers have cutting diameters of between ten (10) and twenty-two (22) millimeters.

* * * * *